United States Patent
Liu et al.

(10) Patent No.: US 11,103,528 B1
(45) Date of Patent: *Aug. 31, 2021

(54) SLOW RELEASE CALCIUM COMPOSITION

(71) Applicant: Government of the United States, as represented by the Secretary of the Air Force, Wright-Patterson AFB, OH (US)

(72) Inventors: Sajid Liu, Corpus Christie, TX (US); Jingbo Liu, Corpus Christie, TX (US); Jeffrey C. Wigle, Universal City, TX (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/001,726

(22) Filed: Aug. 25, 2020

Related U.S. Application Data

(63) Continuation of application No. 16/515,390, filed on Jul. 18, 2019, now abandoned.

(51) Int. Cl.
*A61K 33/06* (2006.01)
*A61K 47/40* (2006.01)
*A61K 33/26* (2006.01)

(52) U.S. Cl.
CPC .............. *A61K 33/06* (2013.01); *A61K 33/26* (2013.01); *A61K 47/40* (2013.01)

(58) Field of Classification Search
CPC ....................................................... A61K 33/06
See application file for complete search history.

(56) References Cited

U.S. PATENT DOCUMENTS

| 5,519,012 A | 5/1996 | Fercej-Temeljotov et al. |
| 2017/0166661 A1 | 6/2017 | Liang et al. |

FOREIGN PATENT DOCUMENTS

| CN | 103169837 A | 6/2013 |
| CN | 103463126 A | 12/2013 |
| CN | 103494836 A | 1/2014 |
| CN | 104173292 A | 12/2014 |
| EP | 0583976 A2 | 2/1994 |
| EP | 0583976 A3 | 8/1994 |

(Continued)

OTHER PUBLICATIONS

Buehler, M.D., Fritz R., Age and Cardiovascular Response Adaptation, Determinants of an Antihypertensive Treatment Concept Primarily Based on Beta-Blockers and Calcium Entry Blockers, Hypertension, 1983, vol. 5, No. 5, pp. 94-100.

(Continued)

*Primary Examiner* — Sarah Alawadi
(74) *Attorney, Agent, or Firm* — AFMCLO/JAZ; James F. McBride

(57) ABSTRACT

A slow-release free calcium composition is disclosed which includes at least one polar solvent, from about 1 μM to about 0.25 M substituted or unsubstituted cyclodextrin molecules, and from about 1 ppm to about 1000 ppm calcium cations. The cyclodextrin molecules each have a toroidal shape with an inner cavity and the calcium cations are encapsulated within the inner cavities of the cyclodextrins molecules. A method for making the composition and a method for administering a slow-release form of calcium to a patient is also disclosed.

9 Claims, 2 Drawing Sheets

(56) References Cited

FOREIGN PATENT DOCUMENTS

| JP | H11201903 A | 7/1999 |
|----|-------------|--------|
| WO | 2017148439 A1 | 9/2017 |

OTHER PUBLICATIONS

Chen, Fannie W., et al., Cyclodestrin Induces Calcium-Dependent Lysosomal Exocytosis, PLoS ONE, Nov. 2010, vol. 5, No. 11, 7 pages.

Connors, Kenneth A., The Stability of Cyclodextrin Complexes in Solution, Chem. Rev., 1997, vol. 97, pp. 1325-1357.

Derakhshanian, Venous, et al., Cyclodextrin Inhibits Calcium Carbonate Crystallization and Scaling, Industrial & Engineering Chemistry Research, 2012, vol. 51, pp. 4463-4465.

Gilar, Martin, et al., Enatiomer separation of dihydropyridine calcium antagonists with cyclodextrins as chiral selectors: structural correlation, Journal of Chromatography B., 1996, vol. 681, pp. 133-141.

Kamitori, Shigehiro, et al., Crystal and Molecular Structures of Double Macrocylic Inclusion Complexes Composed of Cyclodextrins, Crown Ethers, and Cations, J. Am. Chem. Soc., 1987, vol. 109, No. 8, pp. 2409-2414.

Li, Caiming, et al., Calcium Ion Contribution to Thermostability of Cyclodextrin Glycosyltransferase Is Closely Related to Calcium-Binding Site CaII, Journal of Agricultural and Food Chemistry, 2013, vol. 61, pp. 8836-8841.

Mattson, Mark P., et al., A role for Na+-dependent Ca2+ extrusion in protection against neuronal excitoxicity, The FASEB Journal, Sep. 2016, vol. 3, No. 13, pp. 2519-2526.

Mekmene, Omar, et al., Determination of calcium-binding caseims, phosphoserine, citrate and pyrophosphate: A modelling approach using free calcium measurement, Food Chemistry, 2001, vol. 127, pp. 676-682.

Nicolis, I., et al., First Sphere Coordiantion of Divalent Metal Citations by Cyclodextrin: Structure of the B-Cyclodextrin-Calcium Chloride-Water (1/2/11.25) Compound, Acta Cryst., 1996, vol. B52, pp. 122-130.

Nicolis, Ioannis, et al., Molecular composites based on first-sphere coordination of calcium ions by a cyclodextrin, Journal of Physical Organic Chemistry, 2001, vol. 14, pp. 35-37.

Norkus, Eugenijus, Metal ion complexes with native cyclodextrins. An overview, J. Incl. Phenom Macrocycl Chem, 2009, vol. 65, pp. 237-248.

Parekh, Anant B., Slow Feedback Inhibition of Calcium Release-activated Calcium Current by Calcium Entry, Journal of Biological Chemistry, Jun. 1998, vol. 273, No. 24, p. 14925-14932.

Rekharsky, Mikhail, et al., 1:1 and 1:2 Complexation Thermodynamics of y-Cyclodextrin with N-Carbobenzyloxy Aromatic Amino Acids and w-Phenylalkanoic Acids, J. Am. Chem. Soc., 2000, vol. 122, p. 10949-10955.

Shende, Pravin, et al., Novel cyclodextrin nanosponges for delivery of calcium in hyperphosphatemia, International Journal of Pharmaceutics, 2013, vol. 456, pp. 95-100.

Stys, Peter K., et al., Ionic Mechanisms of Anoxic Injury in Mammalian CNS White Matter: Role of Na+ Channels and Na+-Ca2 Exchanger, The Journal of Neuroscience, Feb. 1992, vol. 12, No. 2, pp. 430-439.

Tee, Oswald S., et al., Dissociation constants of host-guest complexes of alkyl-bearing compounds with B-cyclodextrin and "hydroxypropyl-B-cyclodextrin", Can. J. Chem., 1996, vol. 74, pp. 736-744.

Tran, Chieu D., et al., Determination of Binding Constants of Cycoldestrins in Room-Temperature Ionic Liquids by Near-Infrared Spectrometry, Anal. Chem., 2002, vol. 74, pp. 5337-5341.

Versluis, Frank, et al., Shape and Release Control of a Peptide Decorated Vesicle through pH Sensitive Orthogonal Supramolecular Interactions, J. Am. Chem. Soc., 2009, vol. 131, p. 13186-13187.

Wigle, Jeffrey C., et al., Nitric oxide measurements in hTERT-RPE cells and subcellular fractions exposed to low levels of red light, Proceedings and program of the SPIE, vol. 8932-89320D, Feb. 2014.

Yamauchi, Akiyo, et al., Selective Potassium Ion Recognition by Benzo-15-crown-5 Fluoroionophorely-Cyclodextrin Complex Sensors in Water, Anal. Chem., 2000, vol. 72, pp. 5841-5846.

Zhang, Lihua, et al., Hydroxypropyl-B-cyclodextrin functionalized calcium carbonate micro particles as a potential carrier for enhancing oral delivery of water-insoluble drugs, International Journal of Nanomedicine, 2015, vol. 10, pp. 3291-3302.

Mattson, M.P.; Guthrie, P.B.; Kater, S.B.; A role for Na-dependent Ca2 extrusion in protection against neuronal axcitotoxicity\, FASEB J, 1989, 3. 2519-2526.

English Language Translation of Abstract of CN103169837A.
English Language Translation of Abstract of CN103463126A.
English Language Translation of Abstract of CN103494836A.
English Language Translation of Abstract of CN104173292A.
English Language Translation of Abstract of JPH11201903A.

Torre, M; Rodriguez, A. R.; Fulgencio Saura-Calixto, F.; Study of the Interactions of Calcium Ions with Lignin, Cellulose, and Pectin, J. Agrie. FoodChem. 1992,40,1762-1766.

Szejtli, J.; Utilization of Cyclodextrins in Industrial Products and Processes, J. Mater. Chem., 1997, 7(4), 575-587.

Nakai, Y.; Yamamoto, K.; Terada, K.; Akimoto, K.; The Dispersed States of Medicinal Molecules in Ground Mixtures with α- or β-Cyclodextrin, Chem. Pharm. Bull. 1984, 32(2), 685-691.

Mar. 20, 2020 Non-final Office Action For U.S. Appl. No. 16/515,390.
Jun. 16, 2020 Final Office Action For U.S. Appl. No. 16/515,390.

Munro, I. C.; Newburne, P. M.; Young, V. R.; Bar, A.; Safety assessment of y-cyclodextrin ; Regulatory Toxicology and Pharmacology 2004, 39, S3-S13.

SLOW RELEASE CALCIUM COMPOSITION

GOVERNMENT INTEREST

The invention described herein may be manufactured, used, and licensed by or for the Government of the United States for all governmental purposes without the payment of any royalty.

FIELD OF THE INVENTION

The present disclosure relates to compositions for the gradual release of metal ions and more specifically to compositions which provide for the slow release of calcium cations, which may be used in buffers solutions or for therapeutic purposes.

BACKGROUND OF THE INVENTION

The presence of various metal cations such as sodium ($Na^+$), potassium ($K^+$), lithium ($Li^+$), calcium ($Ca^{2+}$), magnesium ($Mg^{2+}$), and iron ($Fe^{2+}$) is essential to the functioning of living tissues. However, tissues may also be damaged if these cations become available to the tissues in excessively large amounts.

In particular, divalent calcium ($Ca^{2+}$) is essential to the proper functioning of various cellular metabolic pathways. Thus, divalent calcium ions are often added to buffers used with tissue cultures, and calcium ions may be administered to medical patients as well. Conventional calcium fomulations such as calcium chloride solution, however, release substantially all the calcium cations into solution immediately. Even though some amount of calcium is essential, this sudden release of a large number of calcium cations may itself lead to stress and/or damage too.

Thus, there is a continuing need for novel compositions of metal cations, such as calcium cations, which provide a slower release of the metal cations, thereby reducing stress to tissues which are exposed to the cations in solution.

SUMMARY OF THE INVENTION

In response to these issues, the present disclosure provides, in a first aspect, a slow-release free calcium composition. In accordance with one embodiment of the present disclosure, this composition includes at least one polar solvent, from about 1 µM to about 0.25 M substituted or unsubstituted cyclodextrin molecules, and from about 1 ppm to about 1000 ppm calcium cations. The cyclodextrin molecules each have a toroidal shape with an inner cavity and the calcium cations are encapsulated within the inner cavities of the cyclodextrin molecules.

In certain embodiments, the at least one polar solvent may be selected from the group consisting of water, alcohols, ammonia, ketones, and carboxylic acids.

According to some embodiments, the cyclodextrin molecules are selected from the group consisting of alpha cyclodextrins molecules, beta cyclodextrin molecules, gamma cyclodextrin molecules, delta cyclodextrin molecules, and mixtures thereof.

In accordance with certain embodiments, at least 0.25 mole percent of the cyclodextrin molecules are substituted by reaction of one or more hydroxyl groups from the cyclodextrin molecules with at least one reactant selected from the group consisting of alkanes, alkenes, alkynes, ketones, aldehydes, carboxylic acids, esters, primary amines, secondary amines, tertiary amines, isocyanates, phosphate esters, toluene, and styrenes.

In certain embodiments, the cyclodextrin molecules are gamma cyclodextrin molecules.

In accordance with certain embodiments, the cyclodextrin molecules and the calcium cations are present in a molar ratio from about 4:1 to about 1:4. According to some embodiments, the cyclodextrin molecules and the calcium cations may be present in a molar ratio from about 2:1 to about 1:2.

In accordance with certain embodiments, the composition also includes at least one additional component selected from the group consisting of ethanol, dimethyl sulfoxide, butanone, isopropanol, n-propanol, acetonitrile, dimethylformamide, polyethylene glycol, tetrahydrofuran, ethyl acetate, dichloromethane, sodium borohydride, alpha-cyclodextrin, beta-cyclodextrin, dextran, gum arabic, gum gar, and triethylene glycol monomethyl ether.

Advantageously, the composition according to the present disclosure has been found to release free calcium cations ($Ca^{2+}$) at a gradual, slow rate. Thus, the composition may be advantageously used in buffer solutions for tissue cultures and/or given to medical patients who may benefit from the administration of a calcium supplement. Because the calcium cations are gradually released, rather than being all immediately released into solution, potential stress to living tissues due to excessive amounts of calcium cations is reduced.

In a second aspect, the present disclosure provides a method for making a slow-release free calcium composition. According to one embodiment, the method includes an initial step of preparing a mixture of substituted or unsubstituted cyclodextrin molecules and calcium chloride in a polar solvent, wherein the cyclodextrin molecules each have a toroidal shape with an inner cavity. According to the method, the calcium cations are encapsulated within the inner cavities of the cyclodextrin molecules by heating the mixture to a temperature from about 50° C. to about 70° C. for a period of time from about 15 minutes to about 45 minutes. Then, chloride anions are removed from the mixture by sublimating chlorine gas from the mixture at a temperature from about 40° C. to about 80° C. for a period of time from about 10 minutes to about 50 minutes.

According to some embodiments, the polar solvent may be selected from the group consisting of water, alcohols, ammonia, ketones, and carboxylic acids.

In certain embodiments, the cyclodextrin molecules are selected from the group consisting of alpha-cyclodextrin molecules, beta cyclodextrin molecules, gamma cyclodextrin molecules, delta cyclodextrin molecules, and mixtures thereof.

According to some embodiments, at least 0.25 mole percent of the cyclodextrin molecules are substituted by reaction of one or more hydroxyl groups from the cyclodextrin molecules with at least one reactant selected from the group consisting of alkanes, alkenes, alkynes, ketones, aldehydes, carboxylic acids, esters, primary amines, secondary amines, tertiary amines, isocyanates, phosphate esters, toluene, and styrenes.

In accordance with certain embodiments, the cyclodextrin molecules are gamma cyclodextrin molecules.

In certain embodiments, the cyclodextrin molecules and the calcium cations are present in a molar ratio from about 4:1 to about 1:4. According to some embodiments, the cyclodextrin molecules and the calcium cations may be present in a molar ratio from about 2:1 to about 1:2.

In certain embodiments, the calcium cation encapsulating is carried out at a temperature from about 50° C. to about 70° C.

In accordance with certain embodiments, the chlorine sublimation is carried out at a temperature from about 60° C. to about 75° C.

In a further aspect, the present disclosure provides a method for administering a slow-release form of calcium to a patient. According to one embodiment, a slow-release free calcium composition is provided, which includes from about 1 µM to about 0.25 M substituted or unsubstituted cyclodextrin molecules, and from about 1 ppm to about 1000 ppm calcium cations. The cyclodextrin molecules in the composition each have a toroidal shape with an inner cavity and the calcium cations are encapsulated within the inner cavities of the cyclodextrin molecules. According to the method, an effective dosage of the slow-release free calcium composition is administered to a patient in need thereof.

In certain embodiments, the patient may be suffering from a condition selected from the group consisting of hypocalcemia, osteomalacia, muscle spasms, leg cramps, hypertension, and osteoporosis.

According to some embodiments, the composition also includes an aqueous solvent.

In certain embodiments, the cyclodextrin molecules are selected from the group consisting of alpha cyclodextrins molecules, beta cyclodextrin molecules, gamma cyclodextrin molecules, delta cyclodextrin molecules, and mixtures thereof.

In accordance with certain embodiments, at least 0.25 mole percent of the cyclodextrin molecules are substituted by reaction of one or more hydroxyl groups from the cyclodextrin molecules with at least one reactant selected from the group consisting of alkanes, alkenes, alkynes, ketones, aldehydes, carboxylic acids, esters, primary amines, secondary amines, tertiary amines, isocyanates, phosphate esters, toluene, and styrenes.

In certain embodiments, the cyclodextrin molecules are gamma cyclodextrin molecules.

According to some embodiments, the cyclodextrin molecules and the calcium cations are present in the composition in a molar ratio from about 4:1 to about 1:4. In certain embodiments, the cyclodextrin molecules and the calcium cations may be present in the composition in a molar ratio from about 2:1 to about 1:2.

In accordance with certain embodiments, the composition also includes at least one additional component selected from the group consisting of ethanol, dimethyl sulfoxide, butanone, isopropanol, n-propanol, acetonitrile, dimethylformamide, polyethylene glycol, tetrahydrofuran, ethyl acetate, dichloromethane, sodium borohydride, alpha-cyclodextrin, beta-cyclodextrin, dextran, gum arabic, gum gar, and triethylene glycol monomethyl ether.

In a different aspect, the present disclosure provides a slow-release metal cation composition. In accordance with one embodiment of the present disclosure, this composition includes at least one polar solvent, a first amount of metal cations, and a second amount of encapsulating molecules. The metal cations are selected from the group consisting of calcium cations, lithium cations, iron cations, and mixtures thereof. The encapsulating molecules are selected from the group consisting of substituted or unsubstituted cyclodextrin molecules, substituted or unsubstituted sesquiterpenes molecules, substituted or unsubstituted porphyrins molecules, substituted or unsubstituted cubanes molecules, substituted or unsubstituted spherical fullerenes molecules, and mixtures thereof. According to the present disclosure, the metal cations and the encapsulating molecules are present in a molar ratio from about 10:1 to about 1:10. Further, the encapsulating molecules each have a shape with an inner cavity and the metal cations are sequestered within the inner cavities of the encapsulated molecules.

In accordance with certain embodiments, the metal cations are calcium cations. In other embodiments, the metal cations are iron cations.

According to some embodiments, the metal cations and the encapsulating molecules are present in a molar ratio from about 4:1 to about 1:4.

In certain embodiments, the encapsulating molecules are selected from the group consisting of alpha cyclodextrins molecules, beta cyclodextrin molecules, gamma cyclodextrin molecules, delta cyclodextrin molecules, and mixtures thereof.

In accordance with certain embodiments, at least 0.25 mole percent of the cyclodextrin molecules are substituted by reaction of one or more hydroxyl groups from the cyclodextrin molecules with at least one reactant selected from the group consisting of alkanes, alkenes, alkynes, ketones, aldehydes, carboxylic acids, esters, primary amines, secondary amines, tertiary amines, isocyanates, phosphate esters, toluene, and styrenes.

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein.

DETAILED DESCRIPTION OF THE INVENTION

In a first aspect, the present disclosure provides a slow-release free calcium composition. In general, this composition may include at least three components: (1) a solvent, (2) cyclodextrin molecules, and (3) calcium cations. As discussed in more detail below, the calcium cations are encapsulated (i.e. caged) within the cyclodextrins molecules.

First, the composition includes at least one solvent, which will make up the majority of the composition, on a weight basis. The at least one solvent is typically a polar solvent, but in some instances, a nonpolar solvent might be used. Suitable solvents for use in the composition include, for example, solvents selected from the group consisting of water, alcohols, ammonia, ketones, carboxylic acids. Particular examples of suitable alcohols, ketones, and acids include methanol, ethanol, isopropanol, butanols, acetone, methyl isopropyl ketone, and acetic acid. In some instances, a mixture of two or more of the aforementioned solvents may be used as well.

In certain embodiments, the solvent is water.

Figure 1:
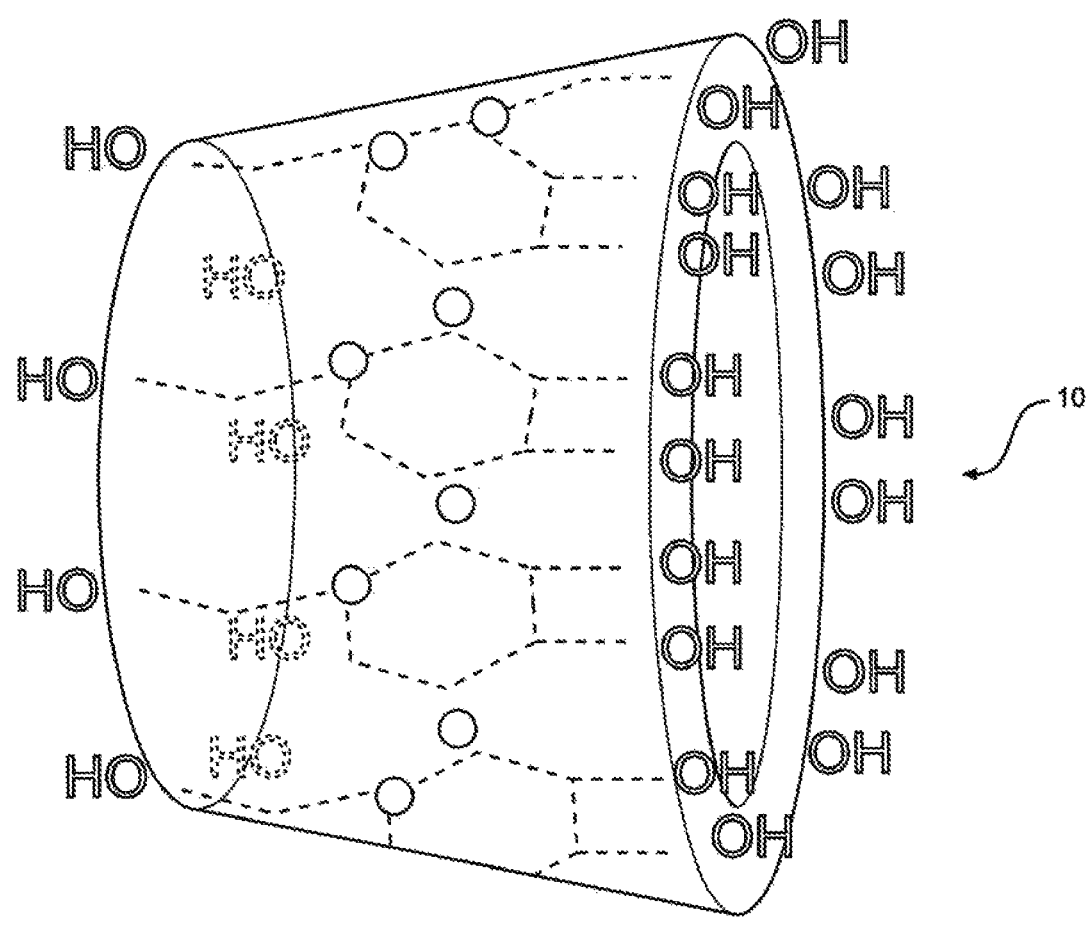
FIG. 1. is a diagram of a cyclodextrin molecule for use according to one embodiment of the present disclosure.

The composition also includes cyclodextrin molecules. Cyclodextrins are a class of oligosaccharide molecules made of glucose units joined together to form a hollow toroidal shape 10, as shown in FIG. 1. The number of glucose units making up the cyclodextrin and the overall size of the cyclodextrin will vary accordingly. According to some embodiments of the present disclosure, the cyclodextrin molecules in the composition may be selected from the group consisting of alpha cyclodextrins molecules (made up of 6 glucose units), beta cyclodextrin molecules (made up of 7 glucose units), gamma cyclodextrin molecules (made up of 8 glucose units), delta cyclodextrin molecules (made up of 9 glucose units), and mixtures thereof. In certain embodiments, the cyclodextrin molecules are more particularly gamma cyclodextrin molecules.

The concentration of cyclodextrin molecules in the composition may vary somewhat but is generally from about 1 µM to about 0.25 M.

Moreover, in certain embodiments of the present disclosure, at least a portion of the cyclodextrin may be functionalized by the inclusion of various substituents which improve the interaction between cyclodextrin and the calcium cations. For instance, in certain embodiments, at least 0.25 mole percent of the cyclodextrin molecules may be substituted by reaction of one or more hydroxyl groups from the cyclodextrin molecules with at least one reactant selected from the group consisting of alkanes, alkenes, alkynes, ketones, aldehydes, carboxylic acids, esters, primary amines, secondary amines, tertiary amines, isocyanates, phosphate esters, toluene, and styrenes.

The composition also includes calcium cations, which in general may be provided by any suitable calcium salt which dissociates in the solvent. For instance, the calcium cations may be provided from a calcium chloride salt. Typically, the amount of calcium cations in the composition is from about 1 ppm to about 1000 parts per million (ppm).

In certain embodiments of the present disclosure, the amounts of both the cyclodextrin molecules and the calcium cations may be controlled, so that the desired ratio of cyclodextrin molecules to calcium cations in the composition is maintained. Thus, in certain embodiments, the cyclodextrin molecules and the calcium cations are present in a molar ratio from about 4:1 to about 1:4. According to some embodiments, the cyclodextrin molecules and the calcium cations may be more particularly present in a molar ratio from about 2:1 to about 1:2.

As noted above, the cyclodextrin molecules each have a generally toroidal shape with an inner hollow or cavity in the center of the molecules. According to the present disclosure, the calcium cations are encapsulated within these inner cavities of the cyclodextrins molecules Moreover, in some instances, the composition may also include one or more additional components. For instance, in certain embodiments, the composition may also include at least one additional component selected from the group consisting of ethanol, dimethyl sulfoxide, butanone, isopropanol, n-propanol, acetonitrile, dimethylformamide, polyethylene glycol, tetrahydrofuran, ethyl acetate, dichloromethane, sodium borohydride, alpha-cyclodextrin, beta-cyclodextrin, dextran, gum arabic, gum gar, and triethylene glycol monomethyl ether.

Advantageously, the composition according to the present disclosure has been found to release free calcium cations ($Ca^{2+}$) at a gradual, slow rate. Thus, the composition may be advantageously used in buffer solutions for tissue cultures and/or given to medical patients who may benefit from the administration of a calcium supplement. Because the calcium cations are gradually released, rather than being all immediately released into solution, potential stress to living tissues due to excessive amounts of calcium cations are reduced.

The present disclosure also provides a method for making the aforementioned a slow-release free calcium composition. In general, this method includes an initial step of preparing a mixture of cyclodextrin molecules and calcium chloride in a solvent, generally a polar solvent. The calcium cations are then encapsulated within inner cavities of the cyclodextrin molecules. Finally, the chloride anions are removed from the mixture by sublimating chlorine gas from the mixture.

Figure 2:
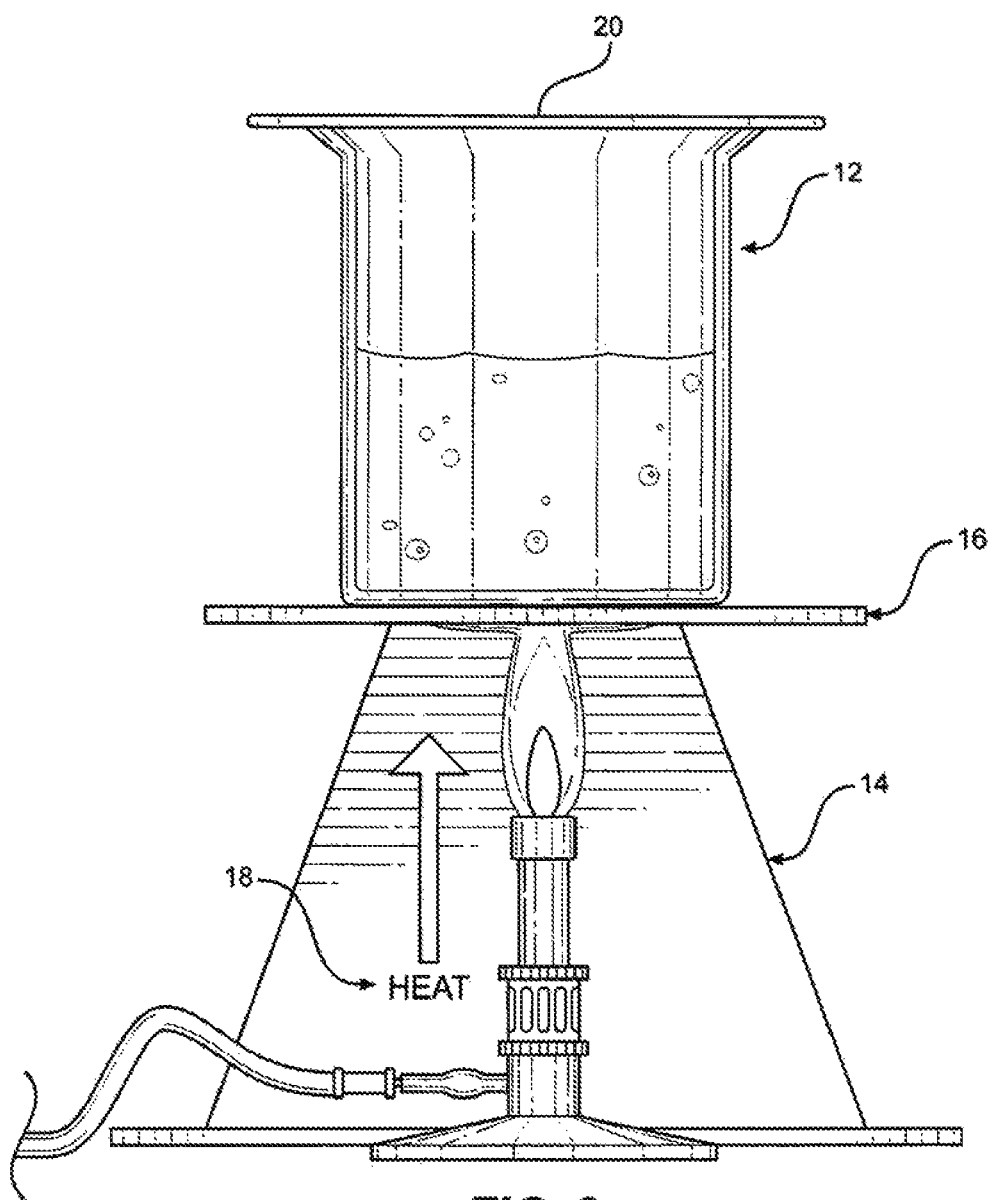
FIG. 2 is a laboratory apparatus for preparing a slow-release free calcium composition according to one embodiment of the present disclosure.

Again, an initial mixture is prepared which includes the solvent, calcium chloride and cyclodextrin molecules. At the lab scale, this may, for instance, be prepared using a beaker 12, as shown in FIG. 2. As discussed above, the solvent is generally a polar solvent and may be selected from the group consisting of water, alcohols, ammonia, ketones, and carboxylic acids. In certain embodiments, the solvent is more particularly water. The cyclodextrin molecules may be substituted or unsubstituted, and generally may be selected from the group consisting of alpha cyclodextrins molecules, beta cyclodextrin molecules, gamma cyclodextrin molecules, delta cyclodextrin molecules, and mixtures thereof. In certain embodiments, the cyclodextrin molecules are more particularly gamma cyclodextrin molecules.

The calcium cations are then encapsulated within the inner cavities of the cyclodextrin molecules. This is accomplished by heating the mixture to a temperature from about 50° C. to about 70° C. for a period of time from about 15 to about 45 minutes. In some instances, the calcium cation encapsulating is more particularly carried out at a temperature from about 50° C. to about 70° C. Again, at this lab scale, this may be accomplished by placing the beaker 12 containing the mixture on a tripod stand 14 with a wire mesh gauze 16 and then heating the beaker using a heat source 18, such as a bunsen burner.

Then, chloride anions are removed from the mixture by sublimating chlorine gas ($Cl_2$) from the mixture. This sublimation is carried out at a temperature from about 40° C. to about 80° C. for a period of time from about 10 minutes to about 50 minutes. In some instances, the chlorine sublimation is more particularly carried out at a temperature from about 60° C. to about 75° C. During the sublimation step, a glass plate 20 may be placed over the beaker 12, so that sublimed chlorine gas may be collected under plate 20, rather than being vented into the air.

In this way, the calcium cations are encapsulated in the cyclodextrin molecules in a free state, i.e., separated from their chloride anions.

In certain embodiments, the cyclodextrin molecules and the calcium cations are present in a molar ratio from about 4:1 to about 1:4. According to some embodiments, the cyclodextrin molecules and the calcium cations may be more particularly present in a molar ratio from about 2:1 to about 1:2.

In a further aspect, the present disclosure also provides a method for administering a slow-release form of calcium to a patient. According to this method, a slow-release free calcium composition, as described above, is provided. This slow-release free calcium composition typically includes from about 1 µM to about 0.25 M substituted or unsubstituted cyclodextrin molecules, and from about 1 ppm to about 1000 ppm calcium cations. The calcium cations are encapsulated within the inner cavities of the cyclodextrins molecules, as previously discussed.

According to the method, an effective dosage of this slow-release free calcium composition is administered to a patient in need thereof. In some instances, this patient may be suffering from a condition selected from the group consisting of hypocalcemia, osteomalacia, muscle spasms, leg cramps, hypertension, and osteoporosis.

In an additional aspect, the present disclosure provides a slow-release metal cation composition. In general, this composition may include at least three components: (1) at least one polar solvent, (2) a first amount of metal cations, and (3) a second amount of encapsulating molecules. According to the present disclosure, the encapsulating molecules each have a shape with an inner cavity and the metal cations are sequestered within the inner cavities of the encapsulated molecules.

The composition first includes at least one solvent, generally a polar solvent. Suitable solvents for use in the composition include, for example, solvents selected from the group consisting of water, alcohols, ammonia, ketones, carboxylic acids. Particular examples of suitable alcohols, ketones, and acids include methanol, ethanol, isopropanol, butanols, acetone, methyl isopropyl ketone, and acetic acid. In some instances, a mixture of two or more of the aforementioned solvents may be used as well. In certain embodiments, the solvent is water.

The composition also includes a first amount of metal cations which are selected from the group consisting of calcium cations, lithium cations, iron cations, and mixtures thereof. In accordance with certain embodiments, the metal cations are calcium cations. In other embodiments, the metal cations are iron cations.

The composition also includes a second amount of encapsulating molecules. These encapsulating molecules are generally selected from the group consisting of substituted or unsubstituted cyclodextrin molecules, substituted or unsubstituted sesquiterpenes molecules, substituted or unsubstituted porphyrins molecules, substituted or unsubstituted cubanes molecules, substituted or unsubstituted spherical fullerenes molecules, and mixtures thereof.

In certain embodiments, the encapsulating molecules are more particularly cyclodextrin molecules, selected from the group consisting of alpha cyclodextrins molecules, beta cyclodextrin molecules, gamma cyclodextrin molecules, delta cyclodextrin molecules, and mixtures thereof.

Moreover, in certain embodiments of the present disclosure, at least a portion of these cyclodextrin molecules may be functionalized by the inclusion of various substituents which improve the interaction between the cyclodextrin and the calcium cations. For instance, in certain embodiments, at least 0.25 mole percent of the cyclodextrin molecules may be substituted by reaction of one or more hydroxyl groups from the cyclodextrin molecules with at least one reactant selected from the group consisting of alkanes, alkenes, alkynes, ketones, aldehydes, carboxylic acids, esters, primary amines, secondary amines, tertiary amines, isocyanates, phosphate esters, toluene, and styrenes.

As noted above, these encapsulating molecules each have a shape with an inner cavity and the metal cations are sequestered within the inner cavities of the encapsulated molecules.

The amounts of the metal cations and the encapsulating molecules may vary somewhat, but in general, the metal cations and the encapsulating molecules are present in a molar ratio from about 10:1 to about 1:10. More particularly, in certain embodiments, the metal cations and the encapsulating molecules are present in a molar ratio from about 4:1 to about 1:4.

EXAMPLES

The following non-limiting examples illustrate various additional aspects of the invention. Unless otherwise indicated, temperatures are in degrees Celsius and percentages are by weight based on the dry weight of the formulation.

Example 1—Preparation of Calcium Ions in Gamma Cyclodextrin

In this example, an inclusion complex of calcium cations encapsulated in gamma-cyclodextrin was prepared. Initially, a 1:1 molar ratio mixture of gamma cyclodextrin (γ-CD) and $CaCl_2$ is first prepared by dissolving 0.25 moles of γ-CD in 10 mL of water, then adding 0.25 moles of $CaCl_2$ with constant stirring in a round bottom sodium borosilicate glass flask. The γ-CD+$CaCl_2$ mixture was then heated at 60° C. and mixed for 35 minutes. A slight color change was observed, indicating completion of the complexation reaction.

Without being bound by theory, it is believed that the γ-CD acts as a reducing and binding agent in the presence of water, where it readily oxidizes the chloride and acts like a Lewis acid.

The mixture is then heated to a temperature of about 60° C., which results, topologically, in the torsional structural opening of both the larger and smaller "faces," of the cyclodextrin, which is then exposed to the solvent; in this case water. The primary and secondary hydroxyl groups are negatively charged and attract the positively charged calcium which becomes encapsulated. In this manner, an inclusion complex is formed that is stable in water and air.

Then, a sublimation procedure is used to remove the chloride anion ($Cl^-$). The γ-CD: $CaCl_2$ inclusion complex is heated to 50° C.-70° C. in a glass beaker closed with a glass plate. The chloride sublimates and collects on the top of the beaker near the glass plate and side wall of the container. To increase the purity of the product, this sublimation process to remove the chloride was repeated three times. The approximate yield of the inclusion complex was 70-78%, recovered as a white-colored crystalline solid.

Example 2—Effect of Calcium Cations on Cellular Nitric Oxide Levels

In this experiment, the influence of $Ca^{2+}$ on nitric oxide (NO) levels was determined by measuring the integrated fluorescence of the reaction product of NO with diaminofluorescein-FM diacetate (DAF-FM DA, $C_{25}H_{18}F_2N_2O_7$).

To demonstrate that NO generated by retinal pigmented epithelium (RPE) cells was related to internal levels of $Ca^{+2}$ ions, RPE wild-type (WT) cells were exposed to red light (RL) having a wavelength (λ) of 635 nm for 15, 30 or 60 minutes, and NO levels were determined by measuring the integrated fluorescence of the reaction product of NO with diaminofluorescein-FM diacetate (DAF-FM DA, $C_{25}H_{18}F_2N_2O_7$), for up to 800 minutes post-exposure.

Procedurally, the experiment was carried out using a 96 well plate, with either ionic calcium ($Ca^{2+}$) or encapsulated calcium (CaCD) added to each of the wells. The concentration of calcium in the wells as $CaCl_2$ was 1.67 mM, and the concentration as CaCD was 2.79 mM stock (or 5 μM final concentration), in a total volume of 300 μL in each well. The number of RPE-WT cells was approximately 175,000 per well. Two reference samples for $CaCl_2$ and CaCD were used to compare relative changes upon exposure to red-light in the presence of $Ca^{2+}$. The RPE cells were incubated with DAF-FM DA for 30 minutes at 37 degrees C. and the fluorescence was immediately measured (as time-point 0 minutes) to obtain a 'background' baseline. The results are shown in the following Table 1:

TABLE 1

Effect of red-light irradiation on NO levels
in retinal pigment epithelium-wild type cells

| WT in PBS + CaCD + RL60 | | WT in PBS + CaCD + RL30 | |
|---|---|---|---|
| Time | Intensity | Time | Intensity |
| 9.3 | 65.89 | 9 | 85.40 |
| 31.3 | 73.26 | 34 | 92.78 |
| 73 | 73.36 | 75 | 105.07 |
| 303.3 | 83.68 | 307.3 | 186.13 |
| 320.3 | 88.60 | 317 | 198.35 |
| 435.6 | 79.12 | 432 | 237.65 |
| 460.3 | 76.74 | 461.3 | 240.16 |
| 778.3 | 133.62 | 768.3 | 465.30 |
| 805.3 | 138.56 | 799.9 | 494.65 |

| WT in PBS + CaCD + RL15 | | WT in PBS + CaCD | |
|---|---|---|---|
| Time | Intensity | Time | Intensity |
| 11.6 | 63.46 | 9.3 | 63.45 |
| 33.9 | 70.83 | 31.3 | 65.94 |
| 75.3 | 70.93 | 73 | 70.92 |
| 308 | 83.69 | 310.6 | 81.26 |
| 320.3 | 88.60 | 317.9 | 88.59 |
| 433 | 93.75 | 430.6 | 91.31 |
| 464.9 | 98.71 | 462.6 | 96.26 |
| 771 | 131.16 | 771 | 116.53 |
| 802.9 | 138.56 | 805.3 | 119.05 |

| WT in PBS + Ca + RL60 | | WT in PBS + Ca + RL30 | |
|---|---|---|---|
| Time | Intensity | Time | Intensity |
| 11.52 | 87.84 | 11.6 | 68.33 |
| 33.54 | 92.78 | 33.6 | 75.70 |
| 72.65 | 105.07 | 72.9 | 73.36 |
| 307.26 | 188.57 | 308 | 83.69 |
| 319.42 | 200.79 | 320.3 | 86.16 |
| 429.53 | 223.01 | 427 | 237.64 |
| 463.82 | 225.53 | 466 | 240.17 |
| 768.4 | 445.79 | 770.9 | 462.87 |
| 799.9 | 480.01 | 799.9 | 494.65 |

| WT in PBS + Ca + RL15 | | WT in PBS + Ca | |
|---|---|---|---|
| Time | Intensity | Time | Intensity |
| 9.09 | 85.40 | 9.09 | 85.40 |
| 28.61 | 95.20 | 28.63 | 92.76 |
| 70.2 | 105.06 | 75.14 | 100.20 |
| 307.22 | 193.44 | 307.24 | 191.01 |
| 316.95 | 203.22 | 319.44 | 198.35 |
| 428.93 | 296.18 | 431.58 | 271.80 |
| 460.74 | 303.57 | 460.95 | 276.75 |
| 765.45 | 506.76 | 770.49 | 489.70 |
| 799.54 | 533.67 | 799.74 | 509.28 |

These results demonstrate that the NO profile determined by the fluorescence of DAF-FM DA remains nearly constant for the various CaCD wells—WT+CaCD (control without red-light exposure); WT+CaCD+RL15; and WT+CaCD+RL60—except for WT+CaCD+RL30. In contrast to the CaCD results, the DAF-FM DA NO profile continued to increase for the ionic calcium wells over the entire 800 minutes. Without being bound by theory, it is believed that these results demonstrate that optimal protection of RPE cells against oxidative stress for the CaCD at RL30 system relative to Ca+RL60 is due to the slow kinetic release of $Ca^{2+}$ from the cyclodextrin cage generating a background concentration that is ideal for the level of oxidative stress. In contrast, higher light levels are required for ionic calcium ions to promote ion release from the mitochondria (inferred) and unnecessary with CaCD+RL60, which becomes saturation and exhibits bimodal behavior, thus for RPW WT cells optimal protection against reactive oxygen species is observed at RL30, for WT RPE cells with ionic calcium at RL60.

From these results, it may be concluded that one source of cellular damage is the rapid fluctuation of calcium from the cytosol to the organelle resulting in ischemic-like stress and cell death, this stoichiometry stimulated using the red light of a specific energy, which itself exhibits bimodal kinetics. Therefore, red light below 0.3 J is insufficient to promote calcium release and no protection is observed and red light above 6 J results in 'excess' calcium to be released, also resulting in minimal cellular protection, the optimal release is calibrated at 3 J. With caged calcium in the form of cyclodextrins, a steady-state equilibrium is set up, enabling lower exposure of red-light and longer protection.

As used herein and in the appended claims, the singular forms "a", "an" and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

While the present invention has been illustrated by the description of one or more embodiments thereof, and while the embodiments have been described in considerable detail, they are not intended to restrict or in any way limit the scope of the appended claim to such detail. Additional advantages and modification will be readily apparent to those skilled in the art. The invention in its broader aspects is therefore not limited to the specific details, representative compositions, and methods and illustrative examples shown and described. Accordingly, departures may be made from such details without departing from the scope or the spirit of the general inventive concept exemplified herein.

What is claimed is:

1. A method for making a free calcium composition, comprising the steps of: a) preparing a mixture of substituted or unsubstituted cyclodextrin molecules and calcium chloride in a polar solvent, wherein the substituted or unsubstituted cyclodextrin molecules each have a toroidal shape with an inner cavity; b) encapsulating calcium cations within the inner cavities of the substituted or unsubstituted cyclodextrin molecules by heating the mixture to a temperature from about 50° C. to about 70° C. for a period of time from about 15 minutes to about 45 minutes; and c) removing chloride anions from the mixture by sublimating chlorine gas from the mixture at a temperature from about 40° C. to about 80° C. for a period of time from about 10 minutes to about 50 minutes.

2. The method of claim 1, wherein the polar solvent is selected from the group consisting of water, alcohols, ammonia, ketones, and carboxylic acids.

3. The method of claim 1, wherein the substituted or unsubstituted cyclodextrin molecules are selected from the group consisting of alpha cyclodextrins molecules, beta cyclodextrin molecules, gamma cyclodextrin molecules, delta cyclodextrin molecules, and mixtures thereof.

4. The method of claim 1, wherein at least 0.25 mole percent of the substituted cyclodextrin molecules are substituted by reaction of one or more hydroxyl groups from the substituted cyclodextrin molecules with at least one reactant selected from the group consisting of alkanes, alkenes, alkynes, ketones, aldehydes, carboxylic acids, esters, primary amines, secondary amines, tertiary amines, isocyanates, phosphate esters, toluene, and styrenes.

5. The method of claim 1, wherein the substituted or unsubstituted cyclodextrin molecules comprise gamma cyclodextrin molecules.

6. The method of claim 1, wherein the substituted or unsubstituted cyclodextrin molecules and the calcium cations are present in a molar ratio from about 4:1 to about 1:4.

7. The method of claim 1, wherein the substituted or unsubstituted cyclodextrin molecules and the calcium cations are present in a molar ratio from about 2:1 to about 1:2.

8. The method of claim 1, wherein the calcium cation encapsulating is carried out at a temperature from about 60° C. to about 70° C.

9. The method of claim 1, wherein the chlorine sublimation is carried out at a temperature from about 60° C. to about 75° C.

* * * * *